(12) United States Patent
Fox (10) Patent No.: US 10,167,125 B2
(45) Date of Patent: Jan. 1, 2019

(54) ARRAY OF BREAKABLE WAX MELTS AND ARRAY OF CONTAINERS FOR BREAKABLE WAX MELTS

(71) Applicant: The Procter & Gamble Company, Cincinnati, OH (US)

(72) Inventor: Sara Elizabeth Fox, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/246,740

(22) Filed: Aug. 25, 2016

(65) Prior Publication Data

US 2018/0057233 A1     Mar. 1, 2018

(51) Int. Cl.

| | |
|---|---|
| *B65D 75/32* | (2006.01) |
| *A61L 9/012* | (2006.01) |
| *B65D 75/56* | (2006.01) |
| *B65D 1/36* | (2006.01) |
| *C11C 5/00* | (2006.01) |
| *C11C 5/02* | (2006.01) |
| *A61L 9/03* | (2006.01) |

(52) U.S. Cl.
CPC .............. *B65D 75/32* (2013.01); *A61L 9/012* (2013.01); *B65D 1/36* (2013.01); *B65D 75/566* (2013.01); *C11C 5/00* (2013.01); *C11C 5/002* (2013.01); *C11C 5/008* (2013.01); *C11C 5/023* (2013.01); *A61L 9/03* (2013.01)

(58) Field of Classification Search
CPC .. B65D 75/32; B65D 75/566; B65D 21/0204; B65D 73/00; B65D 1/36; A61L 9/012; A61L 9/03; C11C 5/008
USPC .............. 206/457, 385, 822, 823, 77.1, 551; 431/295, 288, 289
See application file for complete search history.

(56) References Cited

U.S. PATENT DOCUMENTS

| | | |
|---|---|---|
| 3,730,674 A | 5/1973 | Gross |
| 3,881,682 A * | 5/1975 | Kin .......................... C11C 5/02 249/139 |

(Continued)

FOREIGN PATENT DOCUMENTS

| | | |
|---|---|---|
| JP | 2004035819 A | 2/2004 |
| WO | WO 2015/116528 A1 | 8/2015 |

OTHER PUBLICATIONS

Pan Aroma Scented Wax Melt Vanilla Breeze; available—httpwww.homestoreandmore.iewax-meltspan-aroma-scented-wax-melt-vanilla-breezeinvt063695; Downloaded Jul. 13, 2016.

(Continued)

*Primary Examiner* — J. Gregory Pickett
*Assistant Examiner* — Rafael Ortiz
(74) *Attorney, Agent, or Firm* — Abbey A. Lopez (57) ABSTRACT

An array of breakable wax melts is provided. The array includes a first breakable wax melt having a first shape that corresponds with a first theme. The array also includes a second breakable wax melt having a second shape that is different from the first shape, wherein the second shape corresponds to a second theme. The first and second themes are each selected from the group consisting of: a perfume mixture, holiday, season, a graphic on a container for containing the first or second breakable wax melts, and combinations thereof. An array of containers for containing the breakable wax melts is also provided.

15 Claims, 6 Drawing Sheets

(56) References Cited

U.S. PATENT DOCUMENTS

| | | | |
|---|---|---|---|
| 6,412,640 B1* | 7/2002 | Destanque | A45D 33/28 |
| | | | 132/297 |
| 6,511,313 B1 | 1/2003 | Livne et al. | |
| 2002/0068252 A1* | 6/2002 | Robinson, Jr. | C11C 5/008 |
| | | | 431/289 |
| 2007/0122759 A1 | 5/2007 | Johnson et al. | |
| 2014/0374415 A1* | 12/2014 | Propes | B65D 21/0204 |
| | | | 220/23.8 |
| 2015/0209463 A1* | 7/2015 | Tschantz | C11C 5/023 |
| | | | 220/507 |
| 2017/0209611 A1* | 7/2017 | Banco | A61L 9/012 |

OTHER PUBLICATIONS

All Office Action for U.S. Appl. No. 29/575,434.
All Office Action for U.S. Appl. No. 29/575,435.
All Office Action for U.S. Appl. No. 29/575,436.
All Office Action for U.S. Appl. No. 29/575,437.
All Office Action for U.S. Appl. No. 29/600,263.
All Office Action for U.S. Appl. No. 29/600,265.
EP Search Report; 17187185.8-1106/3287512; 10 Pages dated Mar. 6, 2018.

* cited by examiner

ARRAY OF BREAKABLE WAX MELTS AND ARRAY OF CONTAINERS FOR BREAKABLE WAX MELTS

FIELD

The present disclosure is directed to arrays of breakable wax melts and arrays of containers for containing breakable wax melts.

BACKGROUND

Breakable wax melts are sold in the market today for use in wax melt warmers. Wax melt warmers provide a flameless option for melting scented wax containing perfume. Typical breakable wax melts are formed into a shape that resembles an ice cube tray. Individual wax melts are broken away from the breakable wax melt by a user on an as-needed basis. Breakable wax melts of different scents are typically only distinguishable by the label and/or the color of the breakable wax melt. As such, it would be beneficial to provide features to breakable wax melts that more easily differentiate between different scents or themes of breakable wax melts.

SUMMARY

"Combinations:"

A. An array of breakable wax melts comprising:
  a first breakable wax melt having a first shape that corresponds with a first theme;
  a second breakable wax melt having a second shape that is different from the first shape, wherein the second shape corresponds to a second theme,
  wherein the first and second themes are each selected from the group consisting of: a perfume mixture, holiday, season, a graphic on a container for containing the first or second breakable wax melts, and combinations thereof.
B. The array of Paragraph A, wherein the first and second breakable wax melts have a different perfume mixture.
C. The array of Paragraphs A or B, wherein the first and second breakable wax melts each comprise at least two shaped portions that are joined together along at least one frangible connecting portion.
D. The array of any of Paragraphs A through C, wherein the at least two shaped portions are substantially the same shape.
E. The array of Paragraph D, wherein the at least two shaped portions are substantially the same weight.
F. The array of Paragraphs D or E, wherein the at least two shaped portions have a symmetrical shape.
G. The array of Paragraphs D or E, wherein the at least two shaped portions have an asymmetrical shape.
H. The array of any of Paragraphs A through G, wherein at least two of the shaped portions have different thicknesses.
The array of any of Paragraphs A through H, wherein the first shape is substantially droplet shape and the second shape is a flower.
J. An array of breakable wax melt containers comprising:
  a first container having a first receptacle that is shaped to contain a first breakable wax melt having a first shape that corresponds with a first theme;
  a second container having a second receptacle that is shaped to contain a second breakable wax melt having a second shape that is different from the first shape, wherein the second shape corresponds to a second theme, wherein the first and second receptacles have different shapes, and
  wherein the first and second themes are each selected from the group consisting of: a scent, holiday, season, a graphic on the first or second container, and combinations thereof.
K. An array of products comprising the array of containers of Paragraph J and further comprising:
  the first breakable wax melt contained in the first container;
  the second breakable wax melt contained in the second container.
L. The array of Paragraph J, wherein the first and second breakable wax melts have a different perfume mixture.
M. The array of any of Paragraphs J through L, wherein the first and second breakable wax melts each comprise at least two shaped portions that are joined together along at least one frangible connecting portion.
N. The array of Paragraph M, wherein the at least two shaped portions are substantially the same weight.
O. The array of any of Paragraphs J through N, wherein the first and second containers each comprise a living hinge.

DETAILED DESCRIPTION

The present disclosure is directed to an array of breakable wax melts. The array may include at least two breakable wax melts of different shapes. For example, the array may include a first breakable wax melt having a first shape that corresponds with a first theme. The array may also include at least a second breakable wax melt having a second shape that is different from the first shape, wherein the second shape corresponds to a second theme. The array may include at least two, or alternatively at least three, different shapes of breakable wax melts that each correspond with a different theme.

The themes may each be selected from the group consisting of: a perfume mixture, holiday, season, a graphic on a container for containing the first or second breakable wax melts, and combinations thereof.

The perfume mixture theme may be, for example, floral, oriental, woody, fougère, ambery, woody, leather, chypre, bright floral, green, oceanic/ozone, dune, citrus, the like, and combinations thereof. Each theme may be from the same or different classes of perfume mixtures. For example, two themes may each be floral, but have a different combination of perfume raw materials, such as different floral perfume materials.

A holiday may include, for example, Christmas, Thanksgiving, Hanukah, and the like.

A season may include spring, fall, winter, summer, and combinations thereof.

Each breakable wax melt may be a different color and/or may contain a different perfume mixture.

Each breakable wax melt may comprise at least two shaped portions that are joined together along at least one frangible connecting portion. Each breakable wax melt may comprise at least two shaped portions, alternatively at least three shaped portions, alternatively at least four shaped portions, alternatively at least five shaped portions, alternatively at least six shaped portions, alternatively eight shaped portions. Each breakable wax melt of the array may include the same number of portions or a different number of portions.

The shaped portions of a breakable wax melt may combine to form an overall shape for the breakable wax melt. For example, the breakable wax melt may be shaped as a flower, leaf, fruit, vegetable, droplet, snowman, snowflake, pumpkin, ghost, egg, tree, flag, heart, clover, animal, sun, star, cloud, or various other shapes. The individual shaped portions may be shaped as a flower petal, leaf, slice of fruit, or the like.

The shaped portions may have a regular shape or an irregular shape. Each shaped portion may be the same shape or the shaped portions of an individual breakable wax melt may have different shapes. For example, one breakable wax melt have a droplet shape and another breakable wax melt in the array may be shaped as a flower. In another example, one shape in the array may be one type of flower and a second shape in an array may be a different type of flower.

Each shaped portion of a breakable wax melt may be substantially the same weight. If the shaped portions of a breakable wax melt have different shapes or irregular shapes, the shaped portions within a single breakable wax melt may have different thicknesses to have substantially the same weight. The shaped portions of one breakable wax melt may have substantially the same weight as shaped portions of another breakable wax melt.

The frangible connecting portion or portions of the breakable wax melts is a portion that is less than half of the thickness of the shaped portions. The frangible connecting portions should have a suitable thickness to allow the shaped portions to be separable by the force of a user's hand or hands.

An array of breakable wax melts may be configured in various different ways. For example, an array may include a breakable wax melt having the shape of a flower and a floral perfume mixture, and/or a breakable wax melt having the shape of a piece of produce item (e.g. fruit or vegetable) or the cross-section of a produce item and a perfume mixture that emulates the scent of the particular produce type, and/or a breakable wax melt having a shape such as a snowflake, snowman, tree, pumpkin and the like and a perfume mixture that is associated with holiday smells, such as peppermint, cinnamon, pine, pumpkin, baked goods, and the like.

The breakable wax melts may include various components, including wax, polymers, dyes and/or pigments, perfume mixtures, UV inhibitors, wax hardeners, and the like. Each breakable wax melt in an array may have a different formulation. For example each breakable wax melt may have a different perfume mixture. The breakable wax melts may include up to 20 wt. %, alternatively up to 15 wt. %, by weight of the breakable wax melt, of a perfume mixture.

The breakable wax melts may be contained in a container to form a product. The container may take various different forms, including a plastic blister pack. Blisters packs may include one or two components, such as a front and a back ray that are fixedly or separably joined together. One of the blister pack trays may be plastic and the second blister pack tray may be paper, cardboard, or plastic. Or, both blister pack trays may be plastic. The plastic trays of a blister pack may be made from a formable web, usually a thermoformed plastic.

Separate trays of a container, such as a front tray and a back tray, may be mechanically joined together or sealed with glue or by welding the plastic trays together. The front and back trays of the container may be reconnectable such that a user is able to open the container, remove one or more shaped portions, close the container, and repeat until the shaped portions are gone. Front and back trays may also be joined together at a living hinge to form a clam-shell package that may be open and closed multiple times.

At least one of the trays of the container includes a receptacle for containing the breakable wax melt. The receptacle may be shaped to match the shape of the breakable wax melt. Thus, an array of containers for breakable wax melts may include at least two containers having different shaped receptacles for containing breakable wax melts of different shapes.

The breakable wax melts may be formed in a variety of ways. For example, the wax composition may be melted and poured into the receptacle of the container, such that the breakable wax melt takes the shape of the receptacle. In another process, the wax composition may be pressed into a mold to shape the breakable wax melt.

The plastic material of a blister pack may be transparent, translucent, or opaque. The blister pack may include UV blockers to prevent degradation to light-sensitive trays of the breakable wax melt.

Many blister packaging machines use heat and pressure via a die to form the cavity or pocket from a roll or sheet of plastic. In recent years, improvements in cold forming, specifically allowing steeper depth/angles during forming, which minimizes the amount of material used for each cavity—have helped this technology increase. The main advantages of the plastic-based blister pack are its more compact size compared to cold formed aluminum and it's transparency to see the product.

Figure 1:
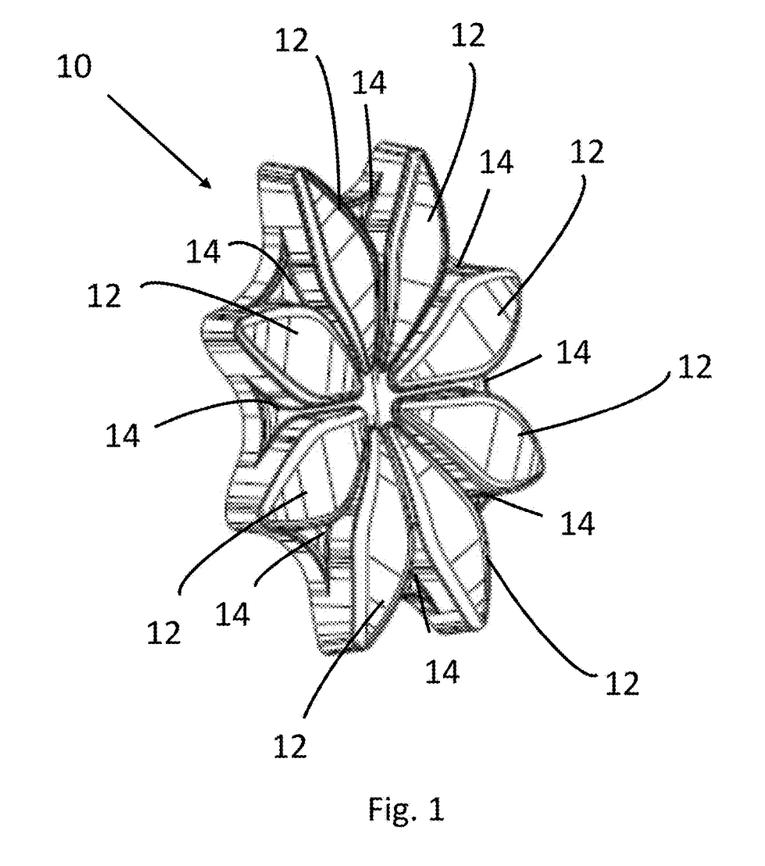
FIG. 1 is a front, perspective view of a breakable wax melt.
Figure 2:
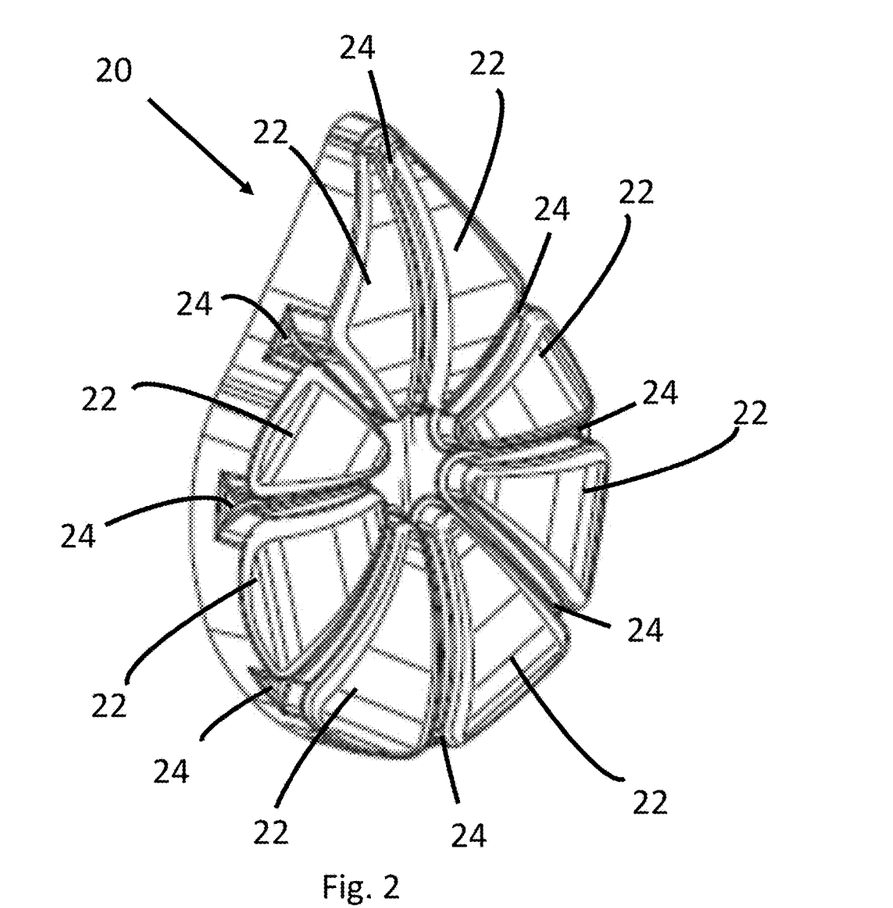
FIG. 2 is a front, perspective view of a breakable wax melt.

FIGS. 1-2 illustrate an exemplary array of breakable wax melts. For example, a first breakable wax melt 10 is shown in FIG. 1. The breakable wax melt 10 of FIG. 1 includes a plurality of shaped portions 12 joined together at frangible connecting portions 14. The shaped portions 12 are shaped as flower petals to form a flower-shaped breakable wax melt 10. The theme of the breakable wax melt may be, for example, a perfume mixture that is flowery and fruity. FIG. 2 shows a second breakable wax melt 20. The second breakable wax melt 20 includes a plurality of shaped portions 22 joined together at frangible connecting portions 24. The shaped portions 22 are asymmetrically shaped and form a droplet-shaped breakable wax melt 20. The theme of the breakable wax melt 20 of FIG. 2 may be a perfume mixture that is fresh and/or airy. FIGS. 1-2 are exemplary breakable wax melts in an array; however, it is to be appreciated that an array of breakable wax melts may include breakable wax melts having various different shapes, sizes, number of shaped portions, colors, perfume mixtures, and combinations thereof.

Figure 3:
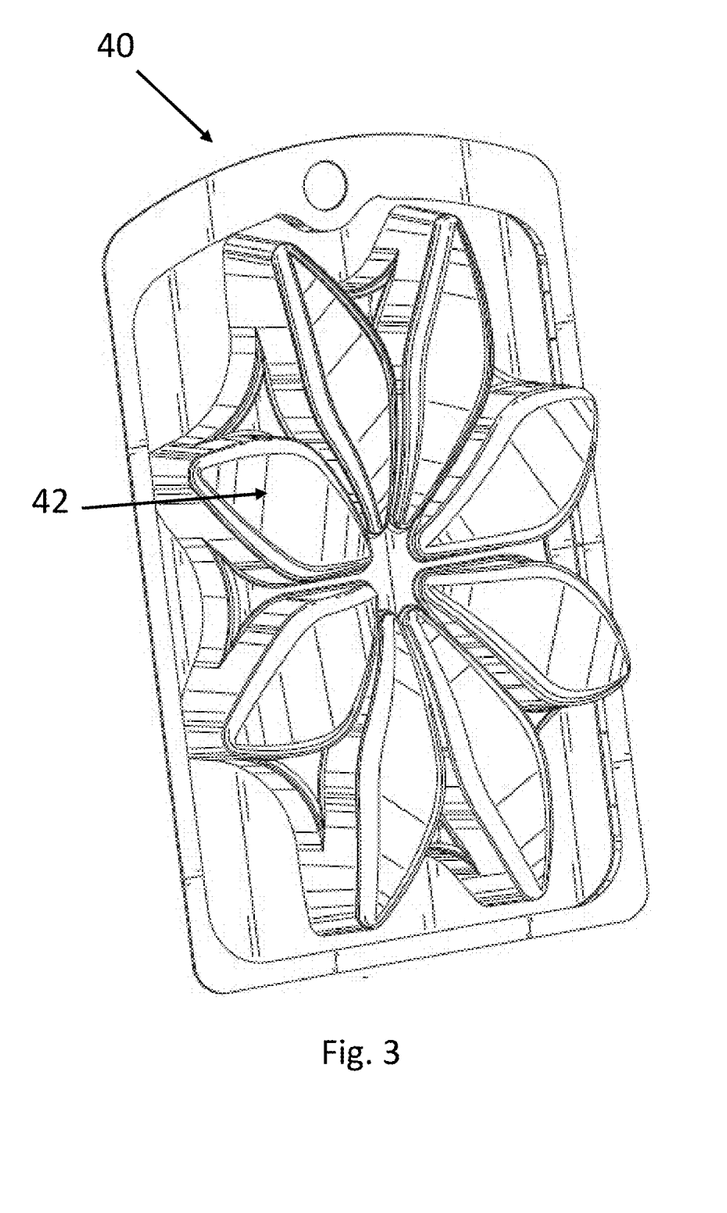
FIG. 3 is a front, perspective view of a tray of a container for a breakable wax melt.
Figure 4:
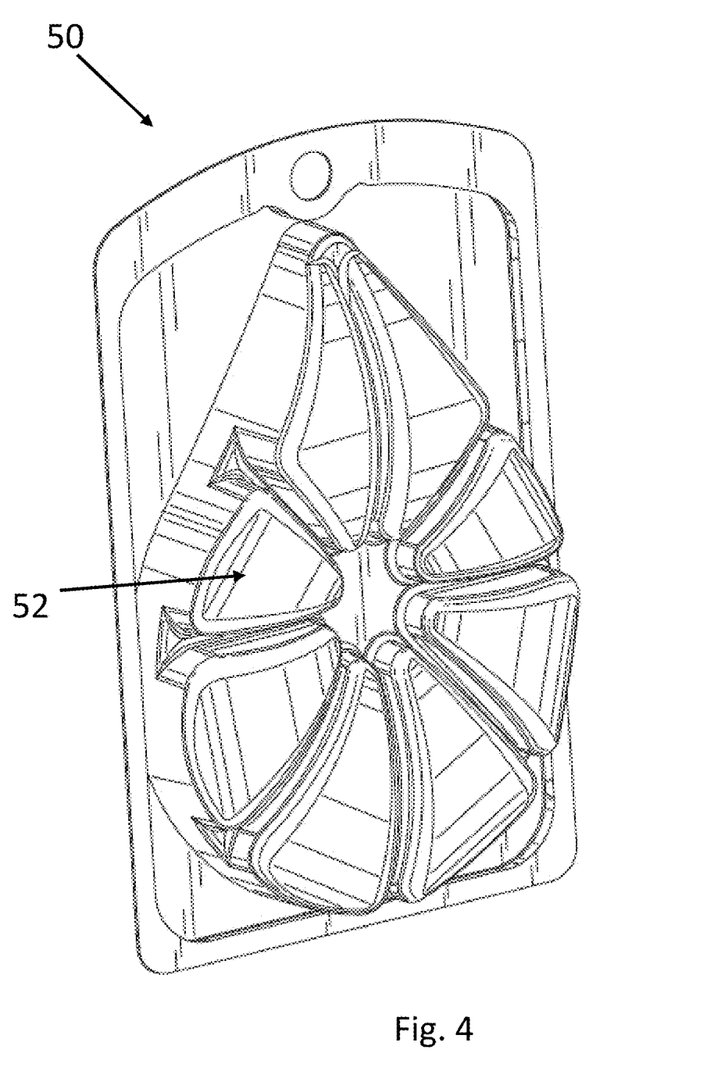
FIG. 4 is a front, perspective view of a tray of a container for a breakable wax melt.
Figure 5:
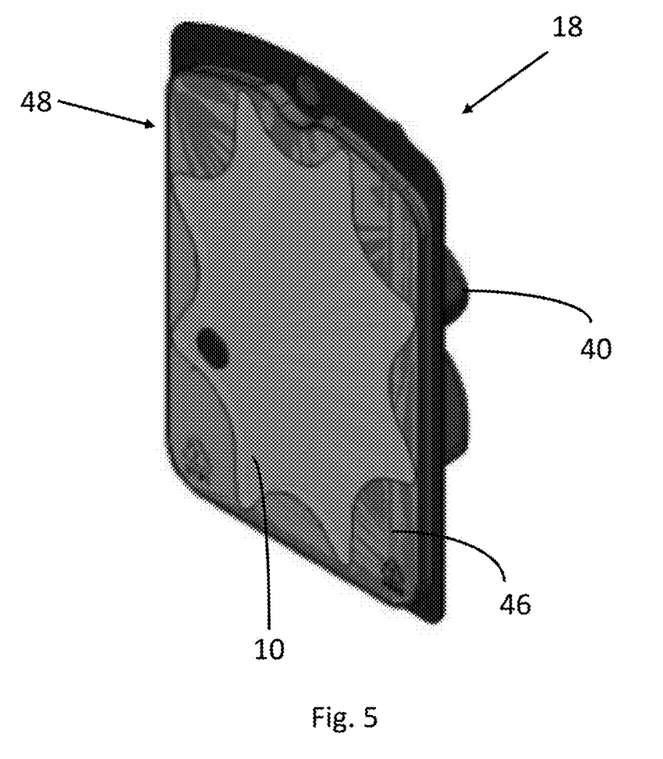
FIG. 5 is a back, perspective view of a product including a container and a breakable wax melt.

FIGS. 3-4 illustrate an exemplary array of trays of containers for containing an array of breakable wax melts. Tray 40 shown in FIG. 3 includes a receptacle 42 for containing a breakable wax melt, such as the breakable wax melt shown in FIG. 1. Tray 40 may be combined with a second tray to form a container. Tray 50 shown in FIG. 4 includes a receptacle 52 for containing a breakable wax melt, such as the breakable wax melt shown in FIG. 2. Tray 50 may be combined with a second tray to form a container FIG. 5 illustrates an exemplary product 18 comprising a container 48 having a first tray 40, a second tray 46, and a breakable wax melt 10.

Figure 6:
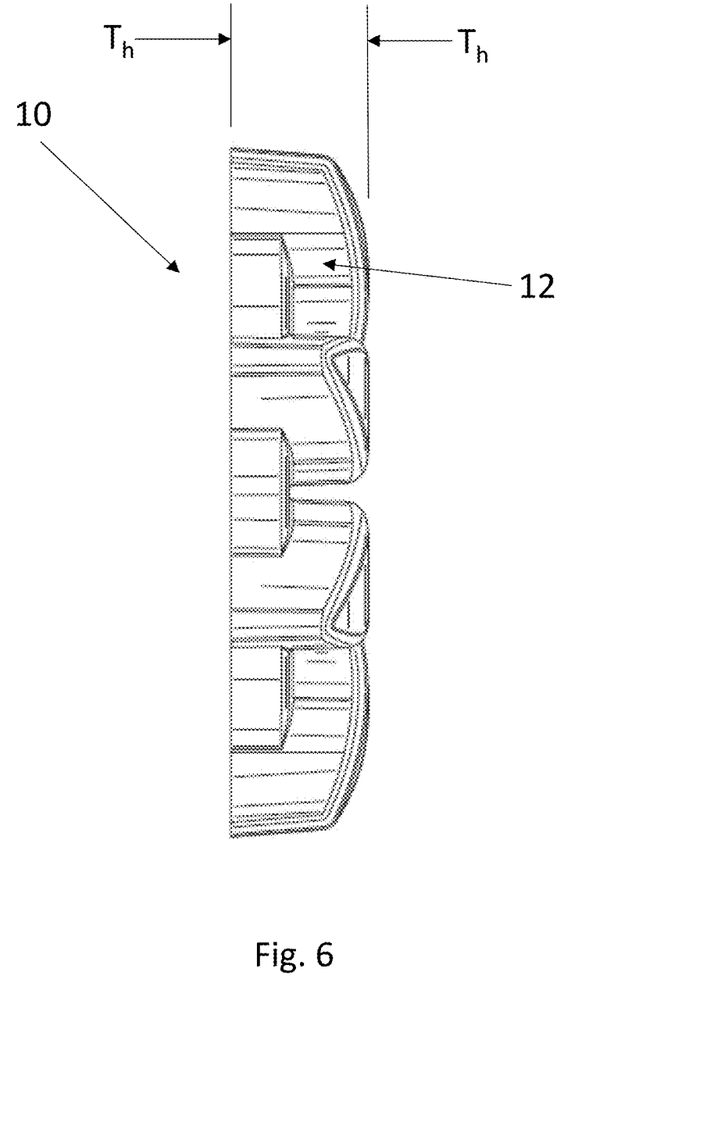
FIG. 6 is a side, elevation view of a breakable wax melt.

As shown in FIG. 6, the breakable wax melt 10 has a thickness $T_h$. The thickness may be uniform for a single shaped portion 12 or the thickness may vary for a single shaped portion 12.

The thickness may be uniform for all shaped portions 12 or may vary across different shaped portions 12 in order to achieve a substantially uniform weight distribution for each shaped portion.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of breakable wax melts comprising:
   a first breakable wax melt disposed in a first container and having a first shape that corresponds with a first theme;
   a second breakable wax melt disposed in a second container that is separate from the first container and having a second shape that is different from the first shape, wherein the second shape corresponds to a second theme,
   wherein the first and second themes are each selected from the group consisting of: a perfume mixture, holiday, season, a graphic on a container for containing the first or second breakable wax melts, and combinations thereof,
   wherein the first and second breakable wax melts comprise different perfume mixtures that correspond with the first and second themes, and
   wherein the first and second breakable wax melts each comprise at least two shaped portions that are joined together along at least one frangible connecting portion, wherein the first and second breakable wax melts are breakable about the frangible connecting portion,
   wherein the shaped portions of the first breakable wax melt have a different shape than the first shape of the first breakable wax melt, and wherein the shaped portions of the second breakable wax melt have a different shape than the second shape of the second breakable wax melt.

2. The array of claim 1, wherein the at least two shaped portions of the first breakable wax melt are substantially the same shape.

3. The array of claim 1, wherein the at least two shaped portions are substantially the same weight.

4. The array of claim 1, wherein the at least two shaped portions of the first breakable wax melt have a symmetrical shape.

5. The array of claim 1, wherein the at least two shaped portions of the second breakable wax melt have an asymmetrical shape.

6. The array of claim 5, wherein at least two of the shaped portions have different thicknesses.

7. The array of claim 1, wherein the first shape is substantially droplet shape and the second shape is a flower.

8. An array of products comprising:
   a first container having a first receptacle that is shaped to contain a first breakable wax melt having a first shape that corresponds with a first theme, the first breakable wax melt is contained in the first container;
   a second container having a second receptacle that is shaped to contain a second breakable wax melt having a second shape that is different from the first shape, wherein the second container is separate from the first container, wherein the second shape corresponds to a second theme, wherein the first and second receptacles have different shapes and wherein the second breakable wax melt is contained in the second container,
   wherein the first and second breakable wax melts each comprise at least two shaped portions that are joined together along at least one frangible connecting portion, wherein the first and second breakable wax melts are breakable about the frangible connecting portion, and
   wherein the first and second themes are each selected from the group consisting of: a scent, holiday, season, a graphic on the first or second container, and combinations thereof,
   wherein the first breakable wax melt has a first perfume mixture corresponding to the first theme, wherein the second breakable wax melt has a second perfume mixture corresponding to the second theme.

9. The array of claim 8, wherein the at least two shaped portions of the first breakable wax melt are substantially the same shape.

10. The array of claim 8, wherein the at least two shaped portions are substantially the same weight.

11. The array of claim 8, wherein the at least two shaped portions of the first breakable wax melt have a symmetrical shape.

12. The array of claim 8, wherein the at least two shaped portions of the second breakable wax melt have an asymmetrical shape.

13. The array of claim 12, wherein at least two of the shaped portions have different thicknesses.

14. The array of claim 8, wherein the first shape is substantially droplet shape and the second shape is a flower.

15. The array of claim 8, wherein the first and second containers each comprise a living hinge.

* * * * *